United States Patent [19]

Brown

[11] Patent Number: 5,522,821
[45] Date of Patent: Jun. 4, 1996

[54] APPARATUS FOR GRASPING A SUTURING DEVICE TO EASE WITHDRAWAL

[76] Inventor: Randall L. Brown, 4637 Chelsea Dr., Baton Rouge, La. 70809

[21] Appl. No.: 417,794

[22] Filed: Apr. 6, 1995

[51] Int. Cl.⁶ .......................... A61B 17/04; A41D 13/08
[52] U.S. Cl. .................. 606/148; 606/1; 2/161.7; 2/163
[58] Field of Search .................. 606/1, 144, 148; 2/160, 163, 167.7

[56] References Cited

U.S. PATENT DOCUMENTS

| | | | |
|---|---|---|---|
| 3,511,242 | 5/1970 | Agnone | 606/148 |
| 4,985,038 | 1/1991 | Lyell | 606/148 |
| 5,140,709 | 8/1992 | Cohn et al. | 2/163 |

*Primary Examiner*—Gary Jackson
*Attorney, Agent, or Firm*—Roy, Kiesel & Tucker

[57] ABSTRACT

A device for gauging the depth of suture penetration and for easing the withdrawal of a suturing device is provided. The device has a sheath with a closed end, where the interior of the sheath is sized to fit over a finger, a plurality of tines positioned on the closed end and a device for firmly holding a suturing device positioned on the closed end. The tines are positioned so that a suturing device has at least one path across the surface of the closed end to the device for firmly holding a suturing device unobstructed by the tines. The sheath is generally constructed of material resistant to puncture or penetration by a suturing device. The device can be incorporated into one fingermember of a glove.

26 Claims, 4 Drawing Sheets

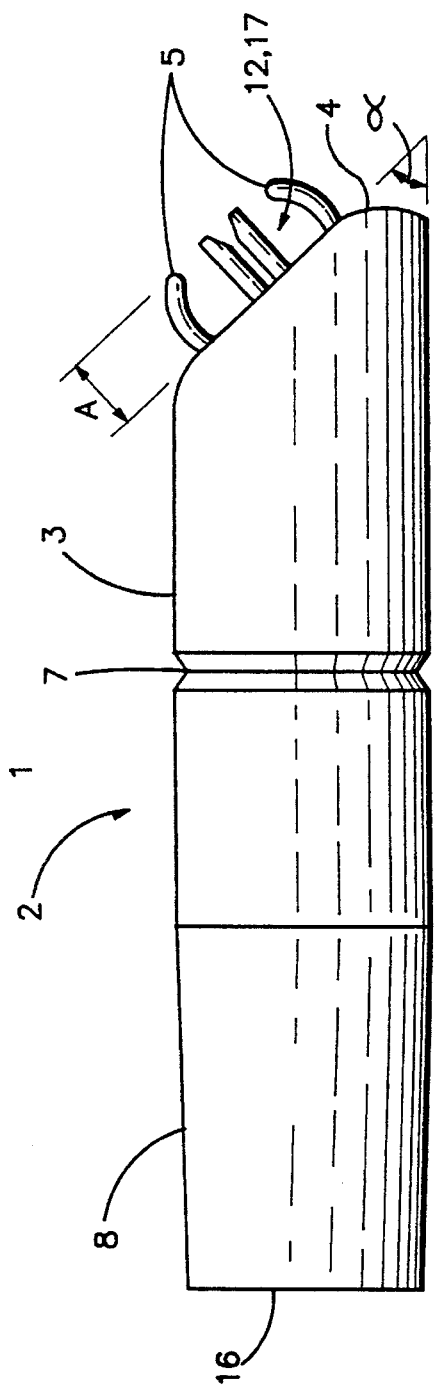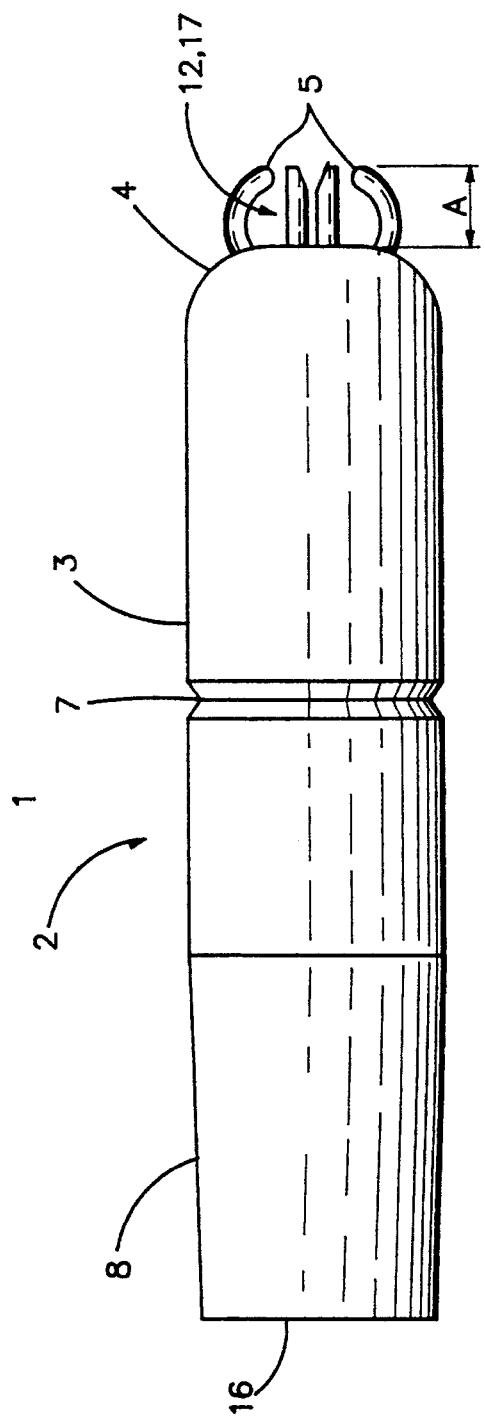

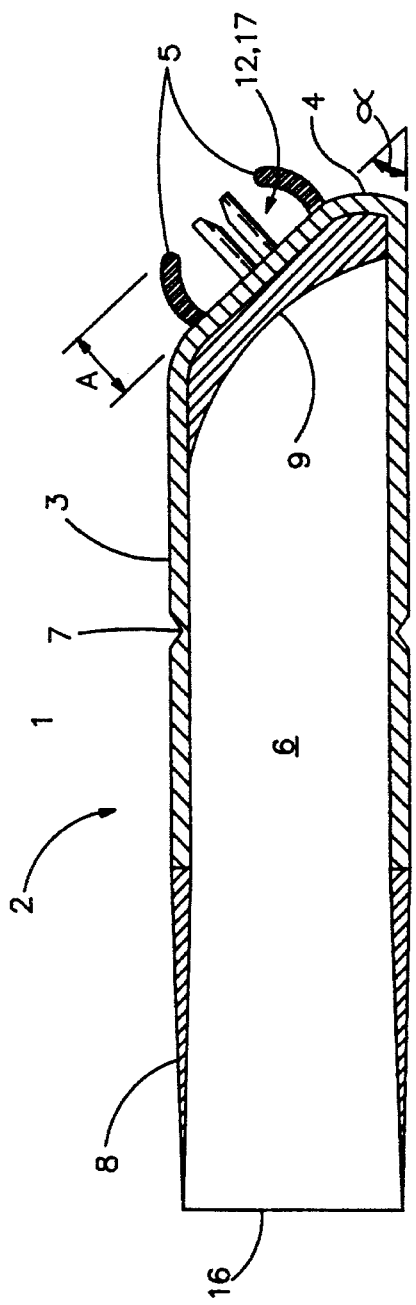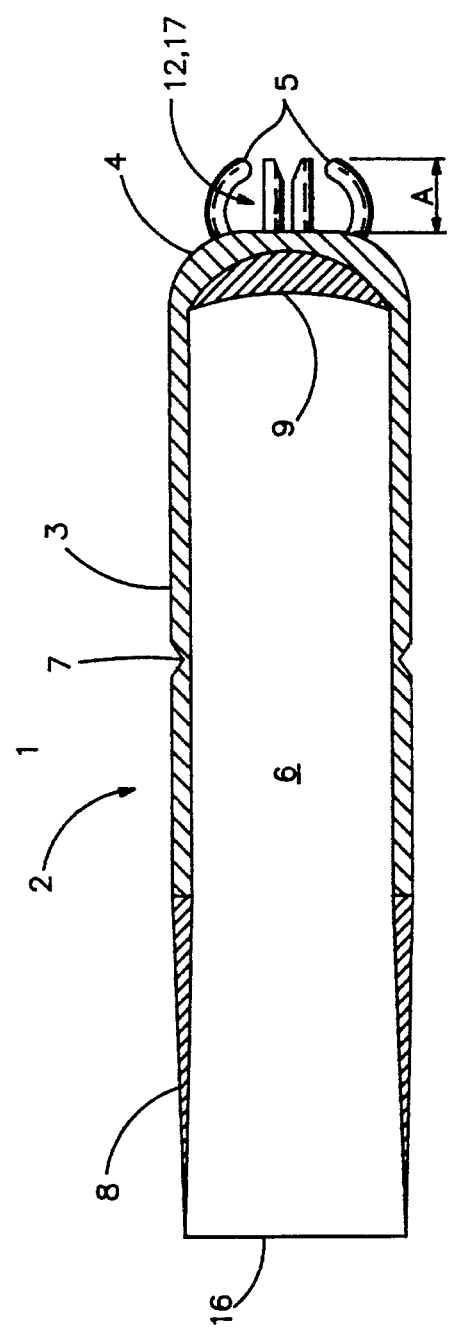

APPARATUS FOR GRASPING A SUTURING DEVICE TO EASE WITHDRAWAL

FIELD OF THE INVENTION

1. Field of the Invention

This invention relates, generally, to devices for placement of sutures in tissues, and more particularly, to devices to help grasp and withdraw a suturing device.

2. Prior Art

In surgery, it is sometimes necessary to attach or suture materials to a first tissue, such materials including: an implanted device, an artificial tissue, a second tissue, or even the first tissue if that first tissue has become torn or separated. The suturing method requires that a suturing device, usually a needle with attached suturing material, first be passed through the material to be attached, and then second, passed into the attachment tissue, thereby joining material and tissue by sutures. The order of the above steps can be reversed.

The required depth of penetration of the suture into the tissue can vary depending upon the materials to be attached, the type of attachment tissue, the thickness of the suturing device and the strength of the attachment desired. The prior methods for gauging the depth of suture penetration depended upon the "look and feel" of the tissues and suture device. That is, in placing the suture, the doctor would position a finger under the attachment tissue and would feel for the needle as it passed into the attachment tissue, the penetration depth being determined by the doctor's subjective estimate based upon the feel of the penetration and by visual inspection, where possible. Because the "look and feel" method is subjective, proper suture depth penetration cannot be consistently or accurately obtained. Further, with the increased concern over communicable blood-borne diseases, the "look and feel" method presents a danger because the suturing device, if depth of penetration is misjudged, can penetrate the doctor's finger causing the doctor's blood to mix with that of the tissue. Thus, caution on the doctor's part is required; however, that caution must be balanced against the need to attain a suture with the desired penetration into the attachment tissue.

Further, the process of extracting the suturing device after the device has passed through tissue requires the surgeon to find and grasp the suturing device and the withdraw the device to prepare for the next suture; often this occurs while retracting tissue with the fingers, making the process of grasping a suturing device with the same fingers both cumbersome and awkward. Further, the suturing device can be hidden from view, requiring the surgeon to find the suturing device by feel, grasp the hidden suturing device, and withdraw the suturing device. Because a suturing device is usually a small diameter needle and, in use, is usually coated with body fluids, finding and then firmly grasping the suturing device can be difficult.

SUMMARY OF THE INVENTION

Therefore, it is an object of the present invention to provide an apparatus which allows an objective assessment of depth of suture penetration.

Another object of the present invention is to provide an apparatus for placement over a finger which creates a barrier resistant to penetration by a suturing device.

Another object of the invention is to provide an apparatus for fixing and grasping the suturing device after penetration of a tissue to enable the suturing device to be easily withdrawn.

These and other objects, advantages, and features of this invention will be apparent from the following descriptions of the invention.

Accordingly, a device for placement over a finger having at least one finger joint is provided comprising an elongated sidewall structured to bend at the finger joint of an inserted finger, a closed end, at least one means for holding a suturing device positioned on the closed end, and tines placed on the closed end and projecting outwardly therefrom. The tine length determines, in part, the depth of penetration of the suture. The sidewall and closed end may be constructed of materials resistant to penetration by a suturing device. The closed end may form an angle other than 90 degrees with the sidewalls.

BRIEF DESCRIPTION OF THE DRAWINGS

FIG. 1 is a side elevation view of an embodiment of the invention.

FIG. 2 is a side elevation view of a second embodiment of the invention.

FIG. 3 is a lengthwise cross sectional view of the embodiment depicted in FIG. 1.

FIG. 4 is a lengthwise cross sectional view of the embodiment depicted in FIG. 2.

DETAILED DESCRIPTION

Figure 6:
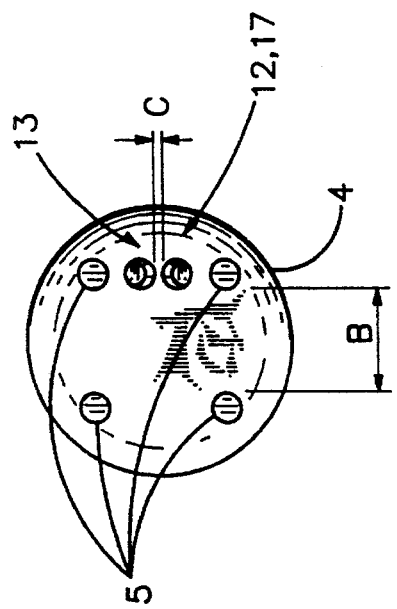
FIG. 6 is an end view of the closed end of a second embodiment of the invention.

As shown generally in FIGS. 1 through 4, the device for gauging suture penetration 1 generally comprised a sheath 2 forming an elongated sidewall 3 and a closed end 4. A plurality of tines 5 are positioned on the closed end 4. The sidewall 3 terminates in an opening 5 opposite the closed end 4. The sidewall 3, the closed end 4, and the opening 5 define an interior 6. The opening 5 and the interior 6 are sized to permit a least one finger joint of a human finger (not shown) to be inserted into the interior 6. The interior 6 can be of varying sizes to accommodate different finger sizes. The sheath 2 may form one fingermember of a surgical glove (not shown).

A resilient layer 9 of material may be disposed on the interior side of the closed end 4 to provide cushioning to the fingertip of the finger inserted in the interior 6. The resilient layer 9 further provides a medium through which a feeling of pressure, exerted by a suturing device on the closed end, may be communicated to the fingertip of the finger inserted into the interior 6. Such a pressure feeling provides feedback to the person wearing the device concerning the degree of penetration of the suturing device through the tissue.

A finger joint area 7 is preferably incorporated into the sidewall 3 adjacent to a finger joint (not shown) of a finger inserted into the interior 6 which allows the finger to flex when inserted in the interior 6. The finger joint area 7 is constructed of a flexible material, such as latex or other flexible plastic, which can be either stretched or compressed without splitting or rupturing. Multiple finger joint areas 7 can be incorporated if the interior 6 is sized to accommodate more than one finger joint.

During surgery, body fluids can migrate into the interior 6, tending to cause the sheath 2 to slip off the inserted finger joint. A finger gripping section 8 constructed of elastic material is preferably incorporated into the elongated sidewall 3 adjacent to the opening 5 to frictionally grip the finger joint, reducing the likelihood of the sheath 2 slipping off the finger joint. If the sheath 2 forms one fingermember of a surgical glove, the remaining glove acts as a finger gripping section 8.

The sheath 2 may be composed, in part, of hardened plastic or lightweight metals to lessen the likelihood of a suturing device (not shown), such as a needle, from penetrating the sheath 2. Any material resistant to needle penetration and suitable for exposure to human tissue could be used for sheath 2 construction. Because the closed end 4 of the sheath 2 is more likely to be exposed to the suturing device, it is preferable that at least the closed end 4 be constructed of hardened plastic or the like. The sheath 2 may also be of multiple layer construction, where at least one layer is constructed of a material substantially resistant to penetration by a suturing device.

As shown in FIGS. 1 and 3, the closed end 4 may form an angle α other than 90 degrees with the sidewall 3. The angle α desired in a particular embodiment of the device will be dependent upon the surgical procedure under consideration. For retro-pubic surgical procedures, an angle α of 30 or 90 degrees has been found suitable. The angle α chosen will depend, in part, on the angle formed between the finger joint and the tissue to be sutured.

Positioned on the closed end 4 are a plurality of tines 5 projecting outwardly from the closed end 4. Preferably, the distance B separating adjacent tines 5 is, at a minimum, sufficient to allow a suturing device to pass unobstructed between adjacent tines 5. The tines 5, when pressed against a tissue (not shown) supports and elevates the tissue in the immediate area of the closed end 4. The height of the elevated tissue above the closed end 4 will depend upon the length A of the tines 5. The desired elevation height will depend on the desired depth of penetration of the suture into the tissue. Where it is desired for the suture to completely penetrate the tissue, a longer tine length A is preferable, with the first tine length A dependent, in part, on the type of suturing device, including the thickness and curvature of the suturing device. For complete penetration of most tissue types, a tine length of 6 mm to 10 mm has been found preferable. When only partial penetration of the suture into the tissue is required, a length in the range of 1 mm to 6 mm has been found preferable.

Figure 8:
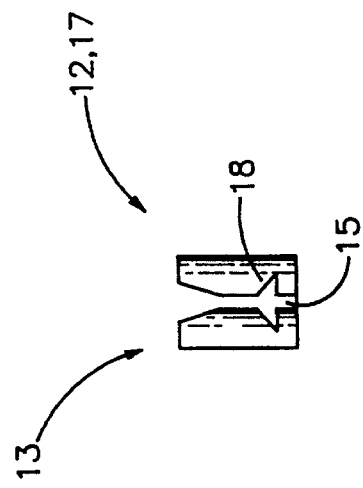
FIG. 8 is a side elevation view of another embodiment of the means for holding a suturing device.
Figure 7:
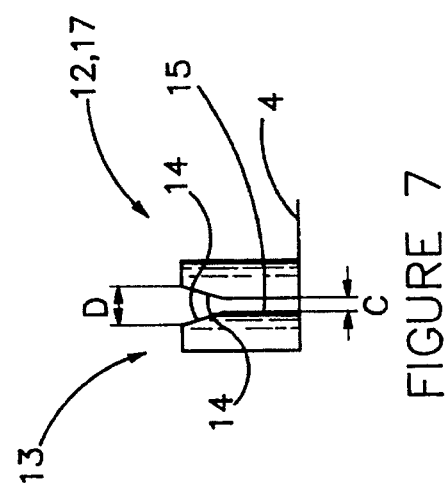
FIG. 7 is a cross sectional view of the closed end showing one embodiment of the means for holding a suturing device.

The device also has a means for firmly holding a suturing device. FIG. 7 shows a sectional view of the preferred means for holding a suturing device; a needle catch 12 having a pair of tapered tines 13 separated a distance C at the closed end 4 to form a needle grasping section 15, where the distance C is less than the thickness of the suturing device (not shown). Each of the pair of tapered tines 13 has a tapered section 14 on the end of tapered tine 13 distant from the closed end 4. The tapered section 14 on each of the tapered tines 13 are opposing, and the distance D between the tapered section 14 has its greatest extent at the ends of the tapered tines 13 distant from the closed end 4. The distance D, at its greatest extent, is sized to be larger than the diameter of a suturing device so that the suturing device can enter the area between the tapered section 14 at the end distant from the closed end 4, be guided down the tapered sections 14, and be snapped into and firmly held in place in needle grasping section 15. The needle grasping section 15 may also have a cutout section 18 to accommodate the cross-sectional shape of the suturing device; such a cutout section to accommodate a triangular cross-sectional shaped needle is shown in FIG. 8. Once the needle is firmly held in the needle catch 12, the needle can be easily removed by simply withdrawing the finger upon which the device is placed.

Figure 5:
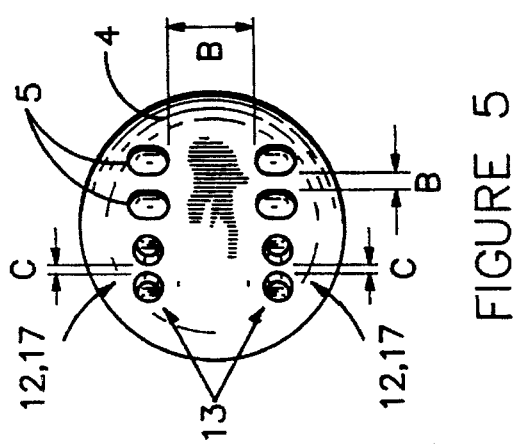
FIG. 5 is an end view of the closed end of an embodiment of the invention.

In any placement of the tines 5, it is important that at least one path across the closed end 4 through the tines 5 be available for a suturing device to pass unobstructed. Further, it is important that a suturing device and be positioned in the needle catch 12 without obstruction by the tines 5. Thus, in a preferred embodiment, the needle catch 12 is positioned on the perimeter of the closed end 4. For instance, as shown in FIG. 5, the tines 5 may be placed in two opposing rows on the closed end 4, with the needle catch 12 positioned between the two opposing rows. Alternatively, as is shown in FIG. 6, the tines 5 may be placed equidistant around the perimeter area of the closed end 4, with the needle catch 12 positioned between adjacent tines 5.

As is shown in FIGS. 1 through 4, the tines 5 may also be arcuate. Arcuate shape tines 5 are less likely to catch and potentially tear tissue, either in use of the device, or in placement or withdrawal of the device. Additionally, each of the pair of tapered tines 13 of the needle catch 12 may be arcuate.

Figure 9:
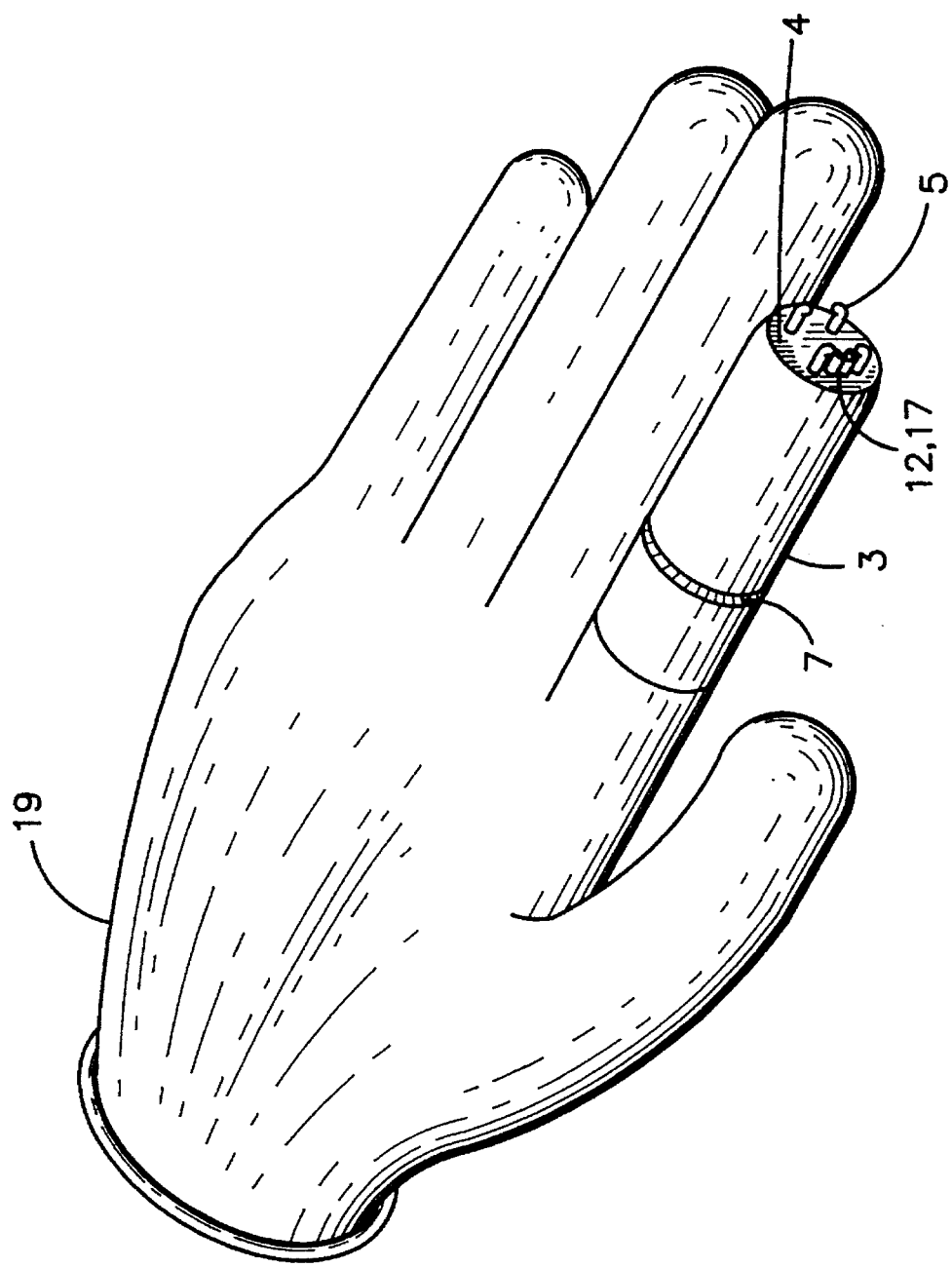
FIG. 9 is a prospective view of the invention as embodied in a glove.

Finally, the entire device can be incorporated into one finger member of a surgical glove as shown in FIG. 9.

There are, of course, many other alternative embodiments and modifications which are intended to be included within the scope of the following claims.

What I claim is:

1. An apparatus to determine the depth to which sutures are placed in tissues and to firmly hold a suturing device, which comprises:

(a) a sheath forming an elongated sidewall and a closed end defining an opening opposite said closed end leading into an interior space, said opening and interior space sized to permit at least a portion of a finger having at least one finger joint to be inserted through said opening and into said interior space; and (b) a plurality of separated tines affixed to and projecting outwardly from said closed end;

(c) at least one means for firmly holding a suturing device, said means positioned on said closed end.

2. An apparatus according to claim 1 where the means for firmly holding a suturing device comprises a needle catch, said needle catch having a pair of tapered tines positioned so that said tapered tines in said needle catch are separated a distance less than the thickness of said suturing device, said distance of separation forming a first gap, each of said tapered tines of said needle catch further having a tapered section at the end of said tapered tines opposite said closed end, where said tapered section on each of said tapered tines in said needle catch are opposing, said opposing tapered sections forming a second gap, said second gap sized at said end of said tapered tines opposite said closed end to enable a suturing device to pass unobstructed, whereby said suturing device can pass into said second gap, be guided down said tapered sections on said tapered tines and be snapped into and firmly held in said first gap.

3. An apparatus according to claim 2 wherein said tapered tines are arcuate in shape.

4. An apparatus according to claim 2 wherein each of said tapered tines further has a cutout section, said cutout sections opposing and said opposing cutout sections shaped to form a cross section of a said suturing device.

5. An apparatus according to claim 4 wherein said cross section is triangular.

6. An apparatus according to claim 1 wherein said elongated sidewall includes at its perimeter area forming said opening a finger gripping section constructed of elastic material which fictionally grips said finger to retard the removal of said finger from said interior space.

7. An apparatus according to claim 1 wherein said closed end is angularly joined to said elongated sidewall.

8. An apparatus according to claim 7 wherein said closed end is joined at an angle of 30 degrees to said elongated sidewall.

9. An apparatus according to claim 7 wherein closed end is joined at an angle of 90 degrees to said elongated sidewall.

10. An apparatus according to claim 1 wherein said elongated sidewall comprises a finger joint area constructed of flexible material and adapted to be positioned opposite said one of said finger joints of said finger.

11. An apparatus according to claim 10 wherein said sheath forms one fingermember of a glove.

12. An apparatus according to claim 1 wherein said closed end is constructed from a material substantially resistant to suturing device puncture.

13. An apparatus according to claim 12 wherein at least that portion of said elongated sidewall adjacent to said closed end is constructed in part from a material substantially resistant to suture needle puncture.

14. An apparatus according to claim 12 wherein said closed end is constructed of at least two layers of material, one of said layers constructed from said material substantially resistant to suture needle puncture.

15. An apparatus according to claim 1 wherein said tines and said means for firmly holding a suturing device are positioned to form at least one path across said closed end, said path being sized to permit a suturing device to pass across said closed end unobstructed by said tines or said means for firmly holding a suturing device.

16. An apparatus according to claim 15 wherein said tines are 1 mm to 10 mm in length.

17. An apparatus according to claim 15 wherein said tines are arcuate in shape.

18. An apparatus according to claim 15 wherein there are an even number of tines.

19. An apparatus according to claim 15 wherein said tines are affixed to the area of said closed end adjacent to said elongated sidewall.

20. An apparatus according to claim 15 wherein said means for firmly holding a suturing device is affixed to the area of said closed end adjacent to said elongated sidewall.

21. An apparatus according to claim 19 wherein said tines are equally spaced from one another.

22. An apparatus according to claim 1 wherein a layer of resilient material is disposed on the interior side of said closed end.

23. On a surgical glove having fingermembers, each fingermember having a closed end, an apparatus to determine the depth to which sutures are placed in tissues and to firmly hold a suturing device which comprises:

(a) a plurality of separated tines affixed to and projecting outwardly from said at least one of said closed ends of said fingermembers;

(b) at least one means for firmly holding a suturing device, said means positioned on said closed end.

24. An apparatus according to claim 23 where the means for firmly holding a suturing device comprises a needle catch, said needle catch having a pair of tapered tines positioned so that said tapered tines in said needle catch are separated a distance less than the thickness of said suturing device, said distance of separation forming a first gap, each of said tapered tines of said needle catch further having a tapered section at the end of said tapered tines opposite said closed end of said fingermember, where said tapered section on each of said tapered tines in said needle catch are opposing, said opposing tapered sections forming a second gap, said second gap sized at said end of said tapered tines opposite said closed end to enable a suturing device to pass unobstructed, whereby said suturing device can pass into said second gap, be guided down said tapered sections on said tapered tines and be snapped into and firmly held in said first gap.

25. An apparatus according to claim 23 wherein said tines and said means for firmly holding a suturing device are positioned to form at least one path across said closed end, said path being sized to permit a suturing device to pass across said end of said fingermember unobstructed by said tines or said means for firmly holding a suturing device.

26. An apparatus to firmly hold a suturing device, which comprises:

(a) a sheath forming an elongated sidewall and a closed end defining an opening opposite said closed end leading into an interior space, said opening and interior space sized to permit at least a portion of a finger having at least one finger joint to be inserted through said opening and into said interior space; and (b) at least one needle catch positioned on said closed end, said needle catch having of a pair of tapered tines positioned so that said tapered tines in said needle catch are separated a distance less than the thickness of said suturing device, said distance of separation forming a first gap, each of said tapered tines of said needle catch further having a tapered section at the end of said tapered tines opposite said closed end, where said tapered section on each of said tapered tines in said needle catch are opposing, said opposing tapered sections forming a second gap, said second gap sized at said end of said tapered tines opposite said closed end to enable a suturing device to pass unobstructed, whereby said suturing device can pass into said second gap, be guided down said tapered sections on said tapered tines and be snapped into and firmly held in said first gap.

* * * * *